(12) United States Patent
Hisanaga et al.

(10) Patent No.: US 8,380,013 B2
(45) Date of Patent: Feb. 19, 2013

(54) CASE IMAGE SEARCH APPARATUS, METHOD AND COMPUTER-READABLE RECORDING MEDIUM

(75) Inventors: Ryuji Hisanaga, Kanagawa (JP); Akira Oosawa, Kanagawa (JP); Masahiro Endo, Shizuoka (JP)

(73) Assignees: FUJIFILM Corporation, Tokyo (JP); Shizuoka Prefecture, Shizuoka (JP)

( * ) Notice: Subject to any disclaimer, the term of this patent is extended or adjusted under 35 U.S.C. 154(b) by 405 days.

(21) Appl. No.: 12/722,291

(22) Filed: Mar. 11, 2010

(65) Prior Publication Data

US 2010/0232661 A1 Sep. 16, 2010

(30) Foreign Application Priority Data

Mar. 12, 2009 (JP) ................................. 2009-059947

(51) Int. Cl.
*G06K 9/00* (2006.01)
*G06K 9/54* (2006.01)
*G06F 7/00* (2006.01)

(52) U.S. Cl. .......................... 382/305; 382/128; 707/769

(58) Field of Classification Search .......... 382/128–134, 382/173, 190, 192, 219, 224, 305, 312; 358/1.9; 707/769–770
See application file for complete search history.

(56) References Cited

U.S. PATENT DOCUMENTS

| 5,319,551 | A | | 6/1994 | Sekiguchi et al. |
| 6,067,369 | A | * | 5/2000 | Kamei .......................... 382/125 |
| 6,687,157 | B1 | * | 2/2004 | Liu et al. ................... 365/185.09 |
| 7,245,747 | B2 | | 7/2007 | Oosawa |
| 7,454,061 | B2 | * | 11/2008 | Yanagisawa et al. .......... 382/181 |
| 7,538,761 | B2 | * | 5/2009 | Nishimura et al. ........... 345/204 |
| 7,564,998 | B2 | * | 7/2009 | Tsujii ............................. 382/128 |
| 8,023,704 | B2 | * | 9/2011 | Oosawa ........................ 382/128 |
| 2008/0212856 | A1 | | 9/2008 | Oosawa et al. |
| 2008/0243395 | A1 | | 10/2008 | Oosawa et al. |
| 2008/0247619 | A1 | | 10/2008 | Li |

FOREIGN PATENT DOCUMENTS

| JP | 2845995 A | 6/1991 |
| JP | 5-250449 A | 9/1993 |
| JP | 3766033 A | 1/2003 |

(Continued)

OTHER PUBLICATIONS

T.F. Cootes, et al., "Active Appearance Models", In Proc. 5th European Conference on Computer Vision, Springer Germany, 1998, pp. 484-498, vol. 2.

(Continued)

*Primary Examiner* — Kanjibhai Patel
(74) *Attorney, Agent, or Firm* — Sughrue Mion, PLLC (57) ABSTRACT

A case image search apparatus according to the presently disclosed subject matter includes: an input unit for inputting a diagnostic object image group from an imaging apparatus; an estimation unit for estimating attributes of a diagnostic object image included in the diagnostic object image group on the basis of the diagnostic object image; a calculation unit for calculating a first feature amount which is a feature amount of the diagnostic object image corresponding to the attribute estimated by the estimation unit; and a search unit for searching a database for a similar case image group similar to the diagnostic object image group by comparing the first feature amount with a second feature amount which is a feature amount of a case image included in the case image group stored in the database corresponding to the attribute estimated by the estimation unit.

15 Claims, 7 Drawing Sheets

FOREIGN PATENT DOCUMENTS

| | | |
|---|---|---|
| JP | 2004-230086 A | 8/2004 |
| JP | 2005-198887 A | 7/2005 |
| JP | 2005-246032 A | 9/2005 |
| JP | 2008-217362 A | 9/2008 |
| JP | 2008-245719 A | 10/2008 |
| JP | 2008-257292 A | 10/2008 |

OTHER PUBLICATIONS

Y.Li, et al., "A Machine learning approach for interactive lesion segmentation", Proceedings of the SPIE, 2007, pp. 651246-1-651246-8, vol. 6512.

* cited by examiner

ESTIMATED REGION OF IA: LIVER

| TEMPORAL PHASE (ESTIMATION) | CHARACTERISTICS |
|---|---|
| WITHOUT CONTRAST MATERIAL | BLOOD VESSEL DENSITY IS LOW, PARENCHYMA DENSITY IS LOW (IA1). |
| ARTERIAL PHASE | ARTERIES DENSITY IS HIGH, PARENCHYMA DENSITY IS LOW (IA2). |
| PORTAL PHASE | PORTAL DENSITY IS HIGH, PARENCHYMA DENSITY IS HIGH (IA3). |

CASE IMAGE SEARCH APPARATUS, METHOD AND COMPUTER-READABLE RECORDING MEDIUM

CROSS-REFERENCE TO RELATED APPLICATIONS

This application claims the priority benefit under 35 U.S.C. §119 of Japanese Patent Application No. 2009-059947 filed on Mar. 12, 2009, which is hereby incorporated in its entirety by reference.

BACKGROUND OF THE INVENTION

1. Field of the Invention

The presently disclosed subject matter relates to a technique of retrieving and presenting a case image similar to an image of a diagnostic object (a diagnostic object image) on the basis of a feature amount extracted from the diagnostic object image.

2. Description of the Related Art

Japanese Patent Application Laid-Open No. 2008-217362 discloses a method of searching for a similar case concerning a liver. The method includes the steps of searching for a similar image imaged under the same imaging condition with respect to each of the imaging conditions in an investigation of the liver; and displaying an image of a case having high degrees of similarity with respect to all the imaging conditions as the similar image.

Japanese Patent Application Laid-Open No. 5-250449 discloses a technique of searching for material having a similar feature on the basis of supplementary information of an image and the feature of the image.

Japanese Patent No. 3766033 discloses a technique of recognizing a positional relationship (imaging direction) of a human body or recognizing an imaging direction and an imaged region (part).

Japanese Patent Application Laid-Open No. 2004-230086 and Japanese Patent No. 2845995 disclose a technique of recognizing blood vessels and organs on the basis of a feature amount such as contours of an image and pixel values.

Japanese Patent Application Laid-Open Nos. 2005-198887 and 2005-246032 disclose a method of automatically extracting a lesion region.

Japanese Patent Application Laid-Open No. 2008-257292 discloses a technique of searching an image concerning a similar case.

Japanese Patent Application Laid-Open No. 2008-245719 discloses a technique of extracting a lesion region on the basis of positional information of a region of interest.

T. F. Cootes, G. J. Edwards, and C. J. Taylor "Active Appearance Models", In Proc. 5th European Conference on Computer Vision, Springer 1998, vol. 2, pp. 484-498, discloses a technique of calculating a feature amount of an image in a region of interest of the image.

SUMMARY OF THE INVENTION

In a technique of searching for an image concerning a similar case in a medical imaging diagnosis, since diagnostic images have different features of cases according to an imaged region and an imaging condition such as with or without contrast material (existence or nonexistence of contrast material). Therefore, it is preferable to search for a diagnostic image based on the imaged region and the imaging condition (See Japanese Patent Application Laid-Open No. 2008-217362). However, the above described technique requires a device for determining a position of a liver and a temporal phase of contrast imaging (a timing of imaging images of an identical imaging position after injection of a contrast agent on time series).

The technique disclosed in Japanese Patent Application Laid-Open No. 5-250449 can be applied to a search refinement based on the supplementary text information of the image. Therefore, the technique disclosed in Japanese Patent Application Laid-Open No. 5-250449 can be used for refining a result of diagnostic image search by using an imaging condition of Japanese Patent Application Laid-Open No. 2008-217362. In order to prepare the supplementary information of the image including information concerning the imaged region and the imaging condition, input operations of a user is required. However, the input operations of the user are burden to the user, and variations and errors can be included in the supplementary information inputted by the user.

The number of imaging conditions can be different on a region-by-region basis. For example, the number of imaging conditions set to image a pulmonary, a liver or a lesion region included therein can be different from each other. There may be regions difficult to be observed under the identical imaging conditions.

The object of the presently disclosed subject matter is to provide an apparatus and a method for automatically estimating attributes of images stored in an image database which can include images of various regions and images imaged under various imaging conditions such as CT (computerized tomography) images and MR (magnetic resonance) images, and searching the image database for a similar image, feature of which is similar to that of an image of interest based on the estimated attribute and outputting a result of the search.

A case image search apparatus according to the presently disclosed subject matter includes: an input unit for inputting a diagnostic object image group from an imaging apparatus; an estimation unit for estimating attributes of a diagnostic object image included in the diagnostic object image group on the basis of the diagnostic object image; a calculation unit for calculating a first feature amount which is a feature amount of the diagnostic object image corresponding to the attribute estimated by the estimation unit; and a search unit for searching a database for a similar case image group similar to the diagnostic object image group by comparing the first feature amount with a second feature amount which is a feature amount of a case image included in the case image group stored in the database corresponding to the attribute estimated by the estimation unit.

The attribute can include information indicating an imaged region of the diagnostic object image.

The estimation unit can estimate the imaged region on the basis of a feature amount pertaining to a pixel value and a shape of the diagnostic object image.

The attribute can include information indicating an imaging condition of the diagnostic object image.

The imaging condition can include information indicating with or without contrast material, or temporal phases of multi-phase imaging.

The search unit can search searches the database for the similar case image group by comparing the feature amount pertaining to at least one of the pixel value and the shape of the diagnostic object image with the feature amount pertaining to at least one of the pixel value and the shape of the case image.

The case image search apparatus can further includes a selection unit for selecting a lesion region from the diagnostic object image, and the search unit can search the database for the similar case image group on the basis of the feature amount pertaining to the lesion region selected by the selection unit The selection unit selects the lesion region on the basis of the amount of the feature pertaining to at least one of the pixel value and the shape of the diagnostic object image.

The case image search apparatus can further includes a display unit for displaying the similar case image group searched by the search unit.

The database can store supplementary information corresponding to the case image, and the display unit can display the supplementary information of the database corresponding to the case image included in the similar case image group.

The display unit can specify a screen layout of the similar case image group corresponding to the attribute estimated by the estimation unit.

The input unit can input the diagnostic object image group from a CT, an MRI or another medical imaging apparatus.

The calculation unit can calculate the first feature amount using a computational expression corresponding to the attribute estimated by the estimation unit.

A case image search method according to the presently disclosed subject matter causes a computer to perform the steps of: inputting a diagnostic object image group from an imaging apparatus; estimating attributes of a diagnostic object image included in the diagnostic object image group on the basis of the diagnostic object image; calculating a first feature amount which is a feature amount of the diagnostic object image corresponding to the estimated attribute; and searching a database for a similar case image group similar to the diagnostic object image group by comparing the first feature amount with a second feature amount which is a feature amount of the case image in the database corresponding to the estimated attribute.

A computer-readable recording medium including instructions stored thereon, such that when the instructions are read and executed by a processor, the processor is configured to perform the steps of: inputting a diagnostic object image group from an imaging apparatus; estimating attributes of a diagnostic object image included in the diagnostic object image group on the basis of the diagnostic object image; calculating a first feature amount which is a feature amount of the diagnostic object image corresponding to the estimated attribute; and searching a database for a similar case image group similar to the diagnostic object image group by comparing the first feature amount with a second feature amount which is a feature amount of the case image in the database corresponding to the estimated attribute.

According to the presently disclosed subject matter, the similar image group is retrieved based on the attribute estimated from the image, thereby allowing the similar image group including images, the attribute of which matches with the attribute of the input image to be retrieved without user's manual registration of the supplementary information of the images such as the imaged region or the imaging condition.

DETAILED DESCRIPTION OF THE PREFERRED EMBODIMENTS

Figure 1:
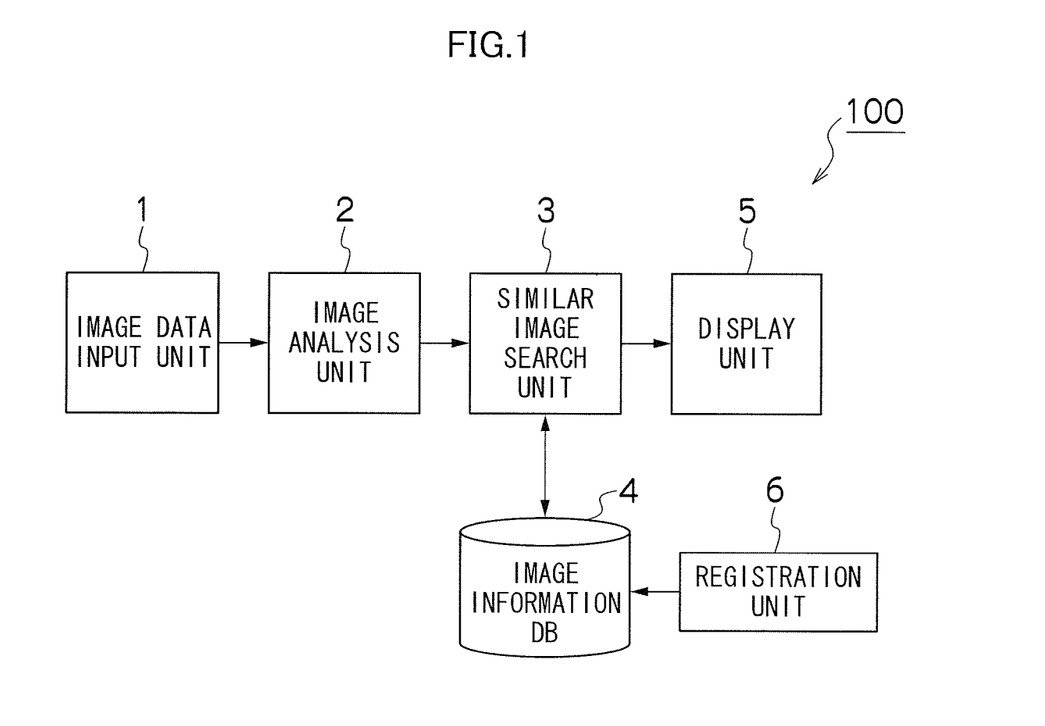
FIG. 1 is a block diagram illustrating a similar case search system.

FIG. 1 is a block diagram illustrating a similar case search system 100 according to an embodiment of the presently disclosed subject matter. The similar case search system 100 includes an image data input unit 1, an image analysis unit 2, a similar image search unit 3, an image information DB (database) 4, a display unit 5, and a registration unit 6. The similar case search system 100 may be configured with a computer including: circuits required for operational processing such as a CPU (central processing unit), RAM (random access memory) and ROM (read-only memory), a data recording medium, a data input and output circuit, a display circuit, an operation device, and a communication circuit.

The individual blocks of the similar case search system 100 may integrally be configured into a computer. Instead, the similar case search system 100 may be configured such that the blocks are configured with respective individual computers and/or logic circuits, and the blocks may be connected to each other via a data communication device such as a network or a system bus. The image analysis unit 2, the similar image search unit 3 and the registration unit 6 may be replaced with program modules (stored in a computer readable medium such as a ROM) to be performed on a computer, and special hardware configurations corresponding to the image analysis unit 2, the similar image search unit 3 and the registration unit 6 are not necessarily required. The display unit 5 may be configured with a liquid crystal display. The image information DB 4 may be configured with a hard disk.

The image data input unit 1 inputs diagnostic object images (query images) obtained by a medical diagnostic imaging apparatus. The diagnostic object images may include a CT image, an MR image, a PET (positron-emission tomography) image, an X ray image (including a CR (computed radiography) image), an US (ultrasonic) image, an endoscopic image, a mammography image, and a pathological image. The image data input unit 1 can input supplementary information such as information about a size of the image and the imaged date and time, and case information, along with these query images. Communication protocols between the image data input unit 1 and the medical diagnostic imaging apparatus and data format of the query images and the supplementary information are compliant with a prescribed standards such as a DICOM (Digital Imaging and Communication in Medicine).

The image analysis unit 2 analyzes a query image inputted from the image data input unit 1, and creates a feature amount (a first feature amount) required to retrieve similar images from case images accumulated in the image information DB 4. A method for creating the first feature amount will be described later.

The similar image search unit 3 compares the first feature amount created by the image analysis unit 2 and the feature amount (second feature amount) of the case image accumulated in the image information DB 4 with each other, and calculates a similarity value indicating a degree of similarity therebetween. The second feature amount may have been preliminarily created from the case image according to a method identical with the calculation method of a first feature amount adopted in the image analysis unit 2, and the second feature amount is accumulated. The similar image search unit 3 identifies the case image whose similarity with the query image is the highest from among all the case images accumulated in the image information DB 4 or the case images corresponding to an imaged region (a liver, a heart, brains, etc.) preliminarily designated by an instruction input from an operation device of the similar case search system 100 based on a result of the comparison performed by the similar image search unit 3. The similar image search unit 3 then displays, on the display unit 5, the identified case image and various types of case information accumulated in the image information DB 4 and corresponding to the case image.

The display unit 5 may be replaced with another output device other than a video output device. For example, the similar case search system 100 may include a printing device for outputting the identified case image and the various types of information corresponding to the case image, which are accumulated in the image information DB 4, instead of the display unit 5 or along with the display unit 5. If a search result does not include image information, the result can be outputted by synthesized voice output and the like from an audio output device. The output device may be a network I/F (interface), and the search result may be outputted to a desired communication terminal (a personal computer, a cellular phone, a PDA (personal digital assistance), etc.).

In the image information DB 4, case information including the case images to be search target images is stored. Here, the case information may be stored in a manner classified according to types of disease. Further, the case information may be linked with statistical information concerning each type of disease, disease information, easily-misdiagnosed disease information concerning an easily-misdiagnosed disease frequently misdiagnosed as a certain type of disease, and medical information.

The case information also includes text-based diagnostic information such as diagnostic reports created by a radiologist in addition to the case image of each definitely diagnosed disease.

The statistical information concerning each type of disease includes, for example, following information:

(a) similarity value of a representative case (the highest similarity in a certain type of disease);

(b) average similarity value;

(c) total number of registered cases of diseases concerned in a case DB;

(d) the number of registered cases similar to the representative cases (case patterns);

(e) characteristics of a case pattern . . . leading symptoms;

(f) characteristics of patients in the case pattern . . . average ages, medical histories, histories of smoking, etc.;

(g) national and regional morbidity rates; and (h) other information.

In the image information DB 4, a feature amount (second feature amount) extracted from a prescribed region of respective registered case images is stored. However, if the case image itself is stored in the image information DB 4, the second feature amount can be acquired by subsequently analyzing the case image by the image analysis unit 2. Accordingly, registration of the second feature amount in the image information DB 4 is not necessarily required to implement of the presently disclosed subject matter.

The display unit 5 may display statistic information such as a similarity image search result for the similar image of each disease in the database, in addition to the image data with a high similarity value, as in Japanese Patent Application Laid-Open No. 2008-257292.

The second feature amount of the case image registered in the image information DB 4 by the registration unit 6 can be acquired by means of image analyses with respect to each region and each imaging condition, as with the image analysis unit 2, which will be described later. The case information corresponding to the case image registered in the image information DB 4 by the registration unit 6 is acquired by a user's input operation to an operation device and the like. The image information DB 4 includes storage areas each corresponding to imaged regions such as a liver, lungs and a heart. The registration unit 6 registers the case image group in the storage area corresponding to an imaged region estimated on the basis of the case image group as with the image analysis unit 2. The divided storage areas may be secured by logically dividing a single recording medium, or by providing physically separate recording media. Implementation of the recording medium physically configuring the image information DB 4 is arbitrary. The recording medium may be configured with a mass recording medium and its readout device, such as a hard disc unit or a DVD (digital versatile disk) recording and readout device.

Figure 2A:
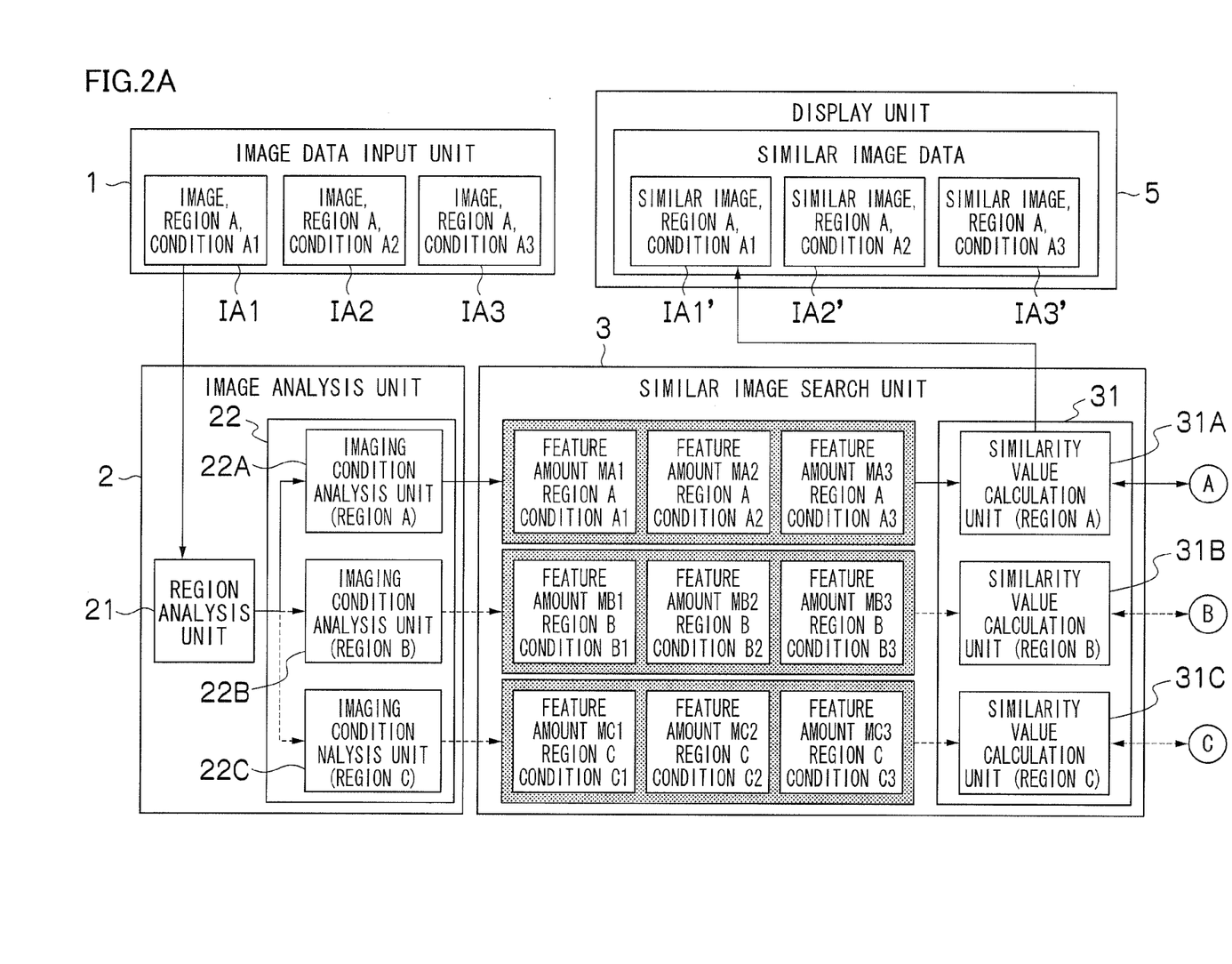
FIGS. 2A and 2B are detailed configuration diagrams of the similar case search system.
Figure 2B:
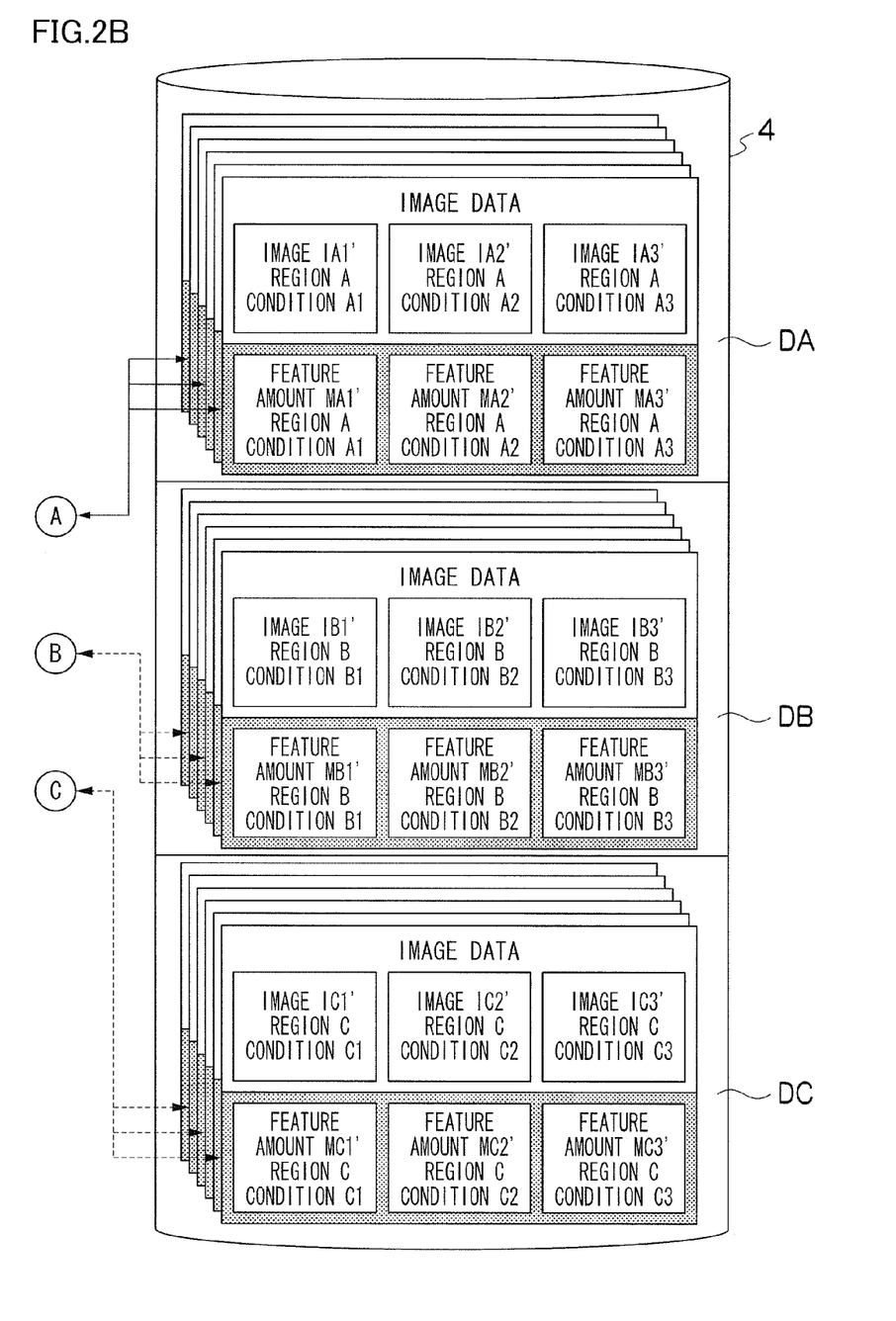

FIGS. 2A and 2B illustrates detailed configurations of the image analysis unit 2 and the similar image search unit 3. Image analysis unit 2 includes a region analysis unit 21, and an imaging condition analysis unit 22 capable of performing imaging condition analyses, on a region-by-region basis, corresponding to the respective different regions. The similar image search unit 3 includes a region-specific similarity value calculation unit 31 corresponding to the respective different regions.

The region analysis unit 21 and the imaging condition analysis unit 22 may be provided with respect to each imaging apparatus which is an input source of a query image group. In this case, the imaging apparatus to be the input source of the query image group is selected according to identification information of the imaging apparatus included in the supplementary information such as a DICOM header or a selection operation inputted to the operation device, the query image group is inputted into the region analysis unit 21 and the imaging condition analysis unit 22 which correspond to the selected imaging apparatus, and the region and the imaging condition are estimated. Here, it is not required to perform the region analyses on all the query images included in the query image group. Instead, if it is estimated that the imaged region is the same and only the imaging conditions of the query images are different from each other based on the supplementary information, the region analysis may be performed on one or only a part of query images. If only one imaging condition is set for a region when imaging an image thereof (for example, as a case of a plain radiographic image of an ankle), estimation of the imaging condition by the imaging condition analysis unit 22 is unnecessary.

FIGS. 2A and 2B illustrates three separate region-specific imaging condition analysis units 22A, 22B and 22C and three region-specific similarity value calculation unit 31A, 31B and 31C. Note that the number of units corresponds to that of the imaged regions, and is not limited to three.

When the image data input unit 1 inputs a group of query images (query image group) corresponding to a plurality of different temporal phases of a specific region(s) (both the singular and the plural acceptable) of a specific patient, the region analysis unit 21 estimates the imaged region corresponding to the query image group. A publicly known image processing technique may be adapted for a recognition process of the imaged region performed by the region analysis unit 21. For example, the estimation is performed using contours of the image, pixel values and characteristics of the positional relationship of organs and the like of a human body in each of the query images configuring the query image group, as in Japanese Patents Nos. 3766033 and 2845995 and Japanese Patent Application Laid-Open No. 2004-230086.

The query image group may include a plurality of query images inputted from the same type of imaging apparatus or include a plurality of query images inputted from different types of imaging apparatuses. For example, a group of four images consisting of two MR images and two CT images of the abdomen of the identical patient may be adopted as the query image group. If images inputted by the different imaging apparatuses are analyzed by the region analysis units 21 and the imaging condition analysis units 22 corresponding to the input imaging apparatuses, and the similar image is retrieved by the similarity value calculation units 31 corresponding to the imaging apparatuses.

FIGS. 2A and 2B illustrate that the query image group IA including three query images IA1 to IA3 corresponding to respective three temporal phases of the region A are inputted into the region analysis unit 21.

Next, the region analysis unit 21 inputs the query image group into the imaging condition analysis unit 22 for analyzing the imaging condition corresponding to the region estimated based on the query image group.

In FIGS. 2A and 2B, the query image group IA corresponding to three temporal phases of the region A is inputted into the region analysis unit 21. If the region analysis unit 21 estimates that the imaged region of the query image group IA is the region A, the region analysis unit 21 inputs the query image group IA into the region-specific imaging condition analysis unit 22A corresponding to the region A. Likewise, if the region analysis unit 21 estimates that the imaged region of a certain query image group is the region B, the region analysis unit 21 inputs the certain query image group into the region-specific imaging condition analysis unit 22B corresponding to the region B. Likewise, if the region analysis unit 21 estimates that the imaged region of a certain query image group is the region C, the region analysis unit 21 inputs the certain query image group into the region-specific imaging condition analysis unit 22C corresponding to the region C. Here, if there are a plurality of query images whose imaged regions are estimated to be identical based on the supplementary information thereof, it is not necessary to perform region analyses on the plurality of query images. Instead, the region analysis may be performed on one of the plurality of query images, and the result of the region analysis may be reflected to all of the plurality of query images of the identical region.

If the estimated region is not identical to the region indicated by the diagnostic information in the header and the like of the query image, the region analysis unit 21 may accept a selection instruction from the operation device indicating an imaging condition analysis unit 22 to which the query image group is inputted, and then the query image group may be inputted into the imaging condition analysis unit 22 which corresponds to the region specified by the selection instruction. This is effective when reliability of the estimation is not high. When an indicator indicating a reliability of the estimation is less than a prescribed threshold, a message including a request for input a selection instruction specifying the region may be displayed on the display unit 5, and the selection instruction may be accepted. Notification of the message is not limited to display. Instead or in addition thereto, the notification may be output of a message voice and the like from a voice output device. The region analysis unit 21 regards the region specified by the selection instruction as the estimated region.

The imaging condition analysis unit 22 estimates the imaging conditions of the query images in the query image group inputted from the region analysis unit 21. The imaging condition analysis unit 22 estimates the imaging conditions on a region-by-region basis. More specifically, the region-specific imaging condition analysis unit 22A estimates the imaging condition of the region A, the region-specific imaging condition analysis unit 22B estimates the imaging condition of the region B, and the region-specific imaging condition analysis unit 22C estimates the imaging condition of the region C.

For example, the region-specific imaging condition analysis unit 22 estimates the imaging condition as follows. First, the region-specific imaging condition analysis unit 22 performs a process of recognizing blood vessels and/or organs imaged in the image. The publicly known image processing technique that performs the recognition on the basis of the feature amount including the contours of object in the images and pixel values can be adopted. The technique disclosed in Japanese Patent Application Laid-Open No. 2004-230086 may be adopted to a recognition process for recognizing the blood vessels, and the technique disclosed in Japanese Patent No. 2845995 may be adopted to a recognition process for recognizing the organs. Instead, the positional relationship of a human body (imaging direction) or imaging direction and imaged region may be recognized by using the technique, for example, disclosed in Japanese Patent No. 3766033, and the imaging direction may be estimated as one of the imaging conditions.

Figure 3:
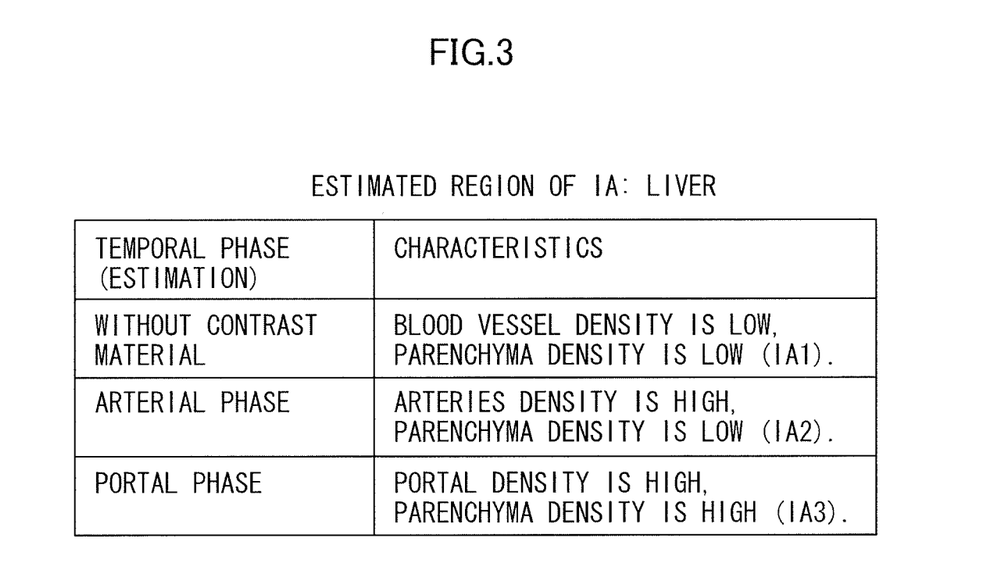
FIG. 3 is a diagram illustrating an example of a temporal phase estimation table.

For example, provided that the query image group IA is a liver CT images, and an image IA1 is a plain CT image, an image IA2 is an arterial phase image, and an image IA3 is a portal phase image. As shown in a temporal phase estimation table of FIG. 3, the region from the query image group IA is estimated as the "liver"; if features of the individual query images IA1 to 1A3 configuring the query image group IA are estimated as "the density of blood vessels is low and the density of parenchyma is low", "the density of arteries is high and the density of parenchyma is low" and "the density of portal vein is high and the density of parenchyma is high", respectively, it is estimated that the imaging condition A1 or the temporal phase of the query image IA1 is "without a contrast material", the imaging condition A2 of the query image IA2 is "arterial phase" and the imaging condition A3 of the query image IA3 is "portal phase". If the query image is a liver CT image, the feature can be determined based on the CT value of each region. The temporal phase estimation table has preliminarily been stored in a storage medium such as the image information DB 4 or an ROM (not illustrated) on a region-by-region basis. The imaging condition analysis unit 22 identifies the imaging condition (temporal phase) which matches with the feature of the individual query image on the basis of the table corresponding to the estimated region, and estimates the identified temporal phase as the imaging condition (temporal phase) of the query image.

The query image groups may include diagnostic images imaged under a plurality of conditions such as lungs, a heart and brains, in addition to the liver. The imaging apparatus is not limited to the CT apparatus. Instead, the imaging apparatus may be various medical imaging apparatuses, such as an MRI apparatus, a PET apparatus, an X-ray apparatus, an US apparatus, an endoscope, a mammography apparatus and a camera for a microscope. Further, the query image groups are not limited to image groups corresponding to a single region. Instead, the query image groups may include image groups corresponding to a plurality of regions. This is because the region analysis unit 21 and the imaging condition analysis unit 22 can individually estimate the region or the imaging condition on each query image.

The region-specific imaging condition analysis unit 22 inputs the query image group into the similarity value calculation unit 31 corresponding to the region estimated from the query image group.

The similarity value calculation units 31 may be provided corresponding to respective imaging apparatuses which are to be input sources of the query image group. In this case, calculation of the similarity value and a search for the similar case image are performed by the similarity value calculation unit 31 corresponding to the selected imaging apparatus.

In FIGS. 2A and 2B, the query image group IA corresponding to three temporal phases of the region A is inputted into the region analysis unit 21. If the region analysis unit 21 estimates that the imaged region of the query image group IA is the region A, the region-specific imaging condition analysis unit 22A inputs the query image group IA into the region-specific similarity value calculation unit 31A corresponding to the region A. Likewise, if the region analysis unit 21 estimates that the imaged region of a certain query image group is the region B, the region-specific imaging condition analysis unit 22B inputs the query image group into the region-specific similarity value calculation unit 31B corresponding to the region B. Likewise, if the region analysis unit 21 estimates that the imaged region of a certain query image group is the region C, the region-specific imaging condition analysis unit 22C inputs the query image group into the region-specific similarity value calculation unit 31C corresponding to the region C.

The similarity value calculation unit 31 calculates the feature amount corresponding to the estimated region and the estimated imaging condition of the query image group inputted from the region analysis unit 21, and compares the similarity value with that of the image data in the image information DB 4. Methods of calculating the feature amount corresponding to the estimated region and the estimated imaging condition are different from each other with respect to each imaging condition corresponding to the estimated region.

The similarity value calculation unit 31 includes a plurality of region-specific similarity value calculation units 31A, 31B and 31C that calculate the feature amounts corresponding to the individual estimated regions and the individual estimated imaging conditions. These units individually calculate the feature amounts with respect to the estimated regions and the estimated imaging conditions. The number of the region-specific similarity value calculation units is not limited to three.

For example, as illustrated in FIGS. 2A and 2B, the region-specific similarity value calculation unit 31A calculates the feature amounts MA1, MA2 and MA3 corresponding to the respective imaging conditions A1, A2 and A3 of the query image IA1 of the region A. Likewise the region-specific similarity value calculation units 31B and 31C calculate the feature amounts MB1, MB2 and MB3; and MC1, MC2 and MC3 corresponding to the respective imaging conditions of the query images of the regions B and C. Although FIGS. 2A and 2B illustrates that three feature amounts are calculated from each of regions A to C, it is not limited to calculate the same number of feature amounts from among different regions; any number of feature amounts may arbitrarily calculated with respect to each region.

The feature amount calculated by the region-specific similarity value calculation unit 31 may be the feature amount pertaining to pixel values such as the average, the variance, the maximum value, the minimum value and the luminance histogram of image data, and/or the feature amount pertaining to the position and/or the shape of the ROI (region of interest) such as the roundness of the contour, the moment thereof, the radius of a section, the volume and the area of the ROI. In addition thereto, the feature amount may be shape information and/or texture information of the lesion in the ROI (region of interest) acquired by the technique disclosed by Cootes et al. shown before. Instead, information temporarily registered in the image information DB 4 may be processed using a prescribed mathematical expression (e.g., principal component analysis and independent component analysis), and the processed result may be adopted as the feature amount. That is, the contour of the image, pixel values, position information and the like acquired by publicly known techniques may be adopted as the feature amount.

A lesion region in the image may be identified in a preprocessing before the calculation of the feature amount, and then the feature amount may be calculated within a scope concerning the lesion region. Specific examples of the identification of lesion regions include methods of automatic calculation such as Japanese Patent Application Laid-Open Nos. 2005-198887 and 2005-246032, and a method of extracting the region on the basis of position information of the region of interest as recited in Japanese Patent Application Laid-Open No. 2008-245719. Upon specifying the lesion region, the imaged region and the imaging condition may be estimated by only analyzing information around the lesion region.

Methods of calculating the feature amounts, which are different from each other with respect to the region and the imaging condition, are prepared in the image information DB 4, a ROM (not illustrated) or the like. For example, in storage areas DA, DB, DC, . . . of the image information DB 4 corresponding to the regions A, B, C, respectively, expressions for calculating the feature amounts of imaging conditions corresponding to the regions A, B, C, . . . , respectively. The region-specific similarity value calculation units 31A, 31B, 31C, . . . read the expressions for calculating with respect to the individual imaging conditions from the storage areas DA, DB, DC, . . . of the corresponding regions, and calculates the feature amounts with respect to each region and each imaging condition on the basis of these expressions.

It is not necessary to identify the lesion region full automatically. Instead, the lesion region may be semi-automatically extracted by means of an image processing technique using the feature amount (a feature amount on pixel values or a feature amount on a shape such as a contour) in the vicinity of the region specified by the user through the operation device. By using the feature amount specialized in the lesion region a case image similar to the lesion region of interest can be searched.

The similar image search unit 3 calculates the similarity value S indicating a degree of correlation between the feature amount of the query image group and the feature amount of the case image group including all the case images accumulated in the image information DB 4 or the case images corresponding to the individual imaging conditions corresponding to the imaged region (a liver, a heart, brains, etc.) preliminarily specified through the operation device.

The calculation of similarity value is performed as follows. First, an individual similarity value Sxn is calculated between the query image corresponding to the individual imaging conditions "n" included in the query image group of the region "x" and the case image corresponding to the individual imaging conditions "n" included in the case image group of the region "x". For example, the region "x" is the liver, and the imaging condition "n" is temporal phases (the plain CT imaging, the arterial phase and the portal phase). The individual similarity value Sxn between the individual query image and the case image may be calculated by means of a publicly known method concerning the feature amount as described above. Typically, the individual similarity value is a least squares distance in a space of feature amount (the value is equal to or more than zero; the nearer to zero the value is, the higher the similarity value is). Here, a feature amount may be normalized, and a specific feature amount may be weighted. Next, a value E acquired by averaging the individual degrees of similarity Sxn corresponding to the respective imaging conditions "n" is adopted as the similarity value "S". The average may be a weighted average instead of a simple average. For example, if a correlation of the portal phase is emphasized, a value of weight corresponding to the portal phase is made to be larger than a value of weight corresponding to another temporal phase.

The method for calculating the similarity value "S" is not limited to above. Instead, the value is arbitrary only if the value is for comprehensively evaluating the correlation between the image groups using the similarity value of the feature amounts between the individual images as a parameter. For example, all the individual degrees of similarity Sxn are simply added and the resultant total sum Σ may be adopted as the similarity value S. Instead, all the individual degrees of similarity Sxn may be multiplied together and the resultant total product Π may be adopted as the similarity value S. Note that a calculation method capable of calculating the similarity value even if the attribute of an image included in the query image group does not match with the attribute of an image included in the case image group may preferably be used. For example, as to the aforementioned weighted average of the individual degrees of similarity, an weight corresponding to an attribute with respect to which the query image group and the case image group do not match with each other is made to be zero.

Provided that the similarity value is the total sum, the average or the weighted average of the similarity value; if the individual similarity value corresponding to any imaging condition is high, the similarity value to the entire query image group becomes high. The similarity value by means of such a calculation method is referred to as a similarity value corresponding to the logical sum of the imaging conditions. Provided that the similarity value is the total product Π of the individual degrees of similarity, if the individual degrees of similarity corresponding to any of imaging conditions are not high, the similarity value to the entire query image group does not become high. The similarity value by means of such a calculation method is referred to as a similarity value corresponding to the logical product of the imaging conditions. The similarity value corresponding to the logical product of the imaging conditions emphasizes the degrees of similarity for the individual image in comparison with the similarity value corresponding to the logical sum of the imaging condition. Accordingly, it is useful for searching for case images similar to each query images. However, if any one of the case images is not similar to the query image, the similarity value plunges, thereby a hit rate of the search decreases. Selection of which method to be used to calculate the similarity value may be made through the operation device, and the similarity value may be calculated according to the selected method. Instead of using all the individual degrees of similarity Sxn, individual degrees of similarity corresponding to a region of imaging conditions designated through the operation device may be eliminated, the similarity value S may be calculated by adding or multiplying the individual degrees of similarity corresponding to the rest of the other imaging conditions not eliminated. According to this, the individual degrees of similarity which has not been added or multiplied are excluded from the criterion for calculating the entire similarity value. For example, the similarity value is calculated by adding or multiplying all the individual degrees of similarity of the temporal phases other than the plain CT, the temporal phases of the plain CT are not to be reflected in a search of the case image group. That is, it is arbitrary to acquire an indication indicating the similarity value between the query image group and the case image group. This is not limited to the method described above.

The similar image search unit 3 ranks (in order) the case image groups on the basis of the similarity value, and identifies the case image group having a rank within a prescribed extent, for example the case image groups within the top fourth rank. The higher the similarity value is, the higher the rank of the case image group becomes. The lower the similarity value is, the lower the rank of case image group becomes. If the degrees of similarity are equal to each other, the ranks are equal to each other. Note that, in order to diversify the information to be outputted as a search result, the number of the case images configuring the case image group is equal to or more than the number of the query images configuring the query image group may be assigned with priority, or a higher rank. The identified case image group is referred to as a similar image group. Individual images configuring the similar image group are referred to as similar images. The similar image search unit 3 displays the similar image group on the display unit 5. Various pieces of case information accumulated in the image information DB 4 and corresponding to the similar image group may be displayed on the display unit 5 together with or instead of the similar image group.

The case images as objects on which the region-specific similarity value calculation units 31A, 31B, 31C, . . . calculate the similarity value S for the query image are limited to those stored in the storage area in the image information DB 4 corresponding to the region estimated from the query image group. For example, the region-specific similarity value calculation unit 31A calculates the similarity value for the query image on the case images stored in the region DA corresponding to the estimated region A. Likewise, the region-specific similarity value calculation unit 31B calculates the similarity value for the query image on the case images stored in the region DB corresponding to the estimated region B; the region-specific similarity value calculation unit 31C calculates the similarity value for the query image on the case images stored in the region DC corresponding to the estimated region C. Since the similar image search unit 3 thus accesses only the case images stored in the storage area corresponding to the estimated region and searches for the similar images, the case images irrelevant to the object region of the query image may not be listed as the search result.

Further, if the region analysis unit 21 and the imaging condition analysis unit 22 are separately provided with respect to each imaging apparatus, the storage areas in the image information DB 4 are divided with respect to each region and each imaging apparatus, and the case images as objects on which the similarity value calculation unit 31 calculates the similarity value S for the query image are limited to those which correspond to the region estimated based on the query image group and stored in the storage area in the image information DB 4 corresponding to the imaging apparatus as the input source of the query image group. This is because the similarity can be calculated only if the images have been taken by the identical imaging apparatus.

The display unit 5 arranges the similar image groups including the similar images corresponding to the respective estimated imaging conditions identified from the storage areas in the image information DB 4 corresponding to the estimated region according to layout information (information specifying a planar arrangement of the images) corresponding to the storage areas concerned. The layout information corresponding to the estimated region has preliminarily been stored in each storage area corresponding to each region of the image information DB 4. The display unit 5 reads the layout information and arranges the similar image groups. The contents of the layout information are arbitrary, and can arbitrarily be created, deleted and updated through the operation device.

For example, it is assumed that the region estimated from the query image group IA (IA1 to IA4) is a liver, the imaging condition A1 estimated from the query image IA1 is a plain CT, the imaging condition A2 estimated from the query image IA2 is an arterial phase, the imaging condition A3 estimated from the query image IA3 is a portal phase, and the imaging condition A4 estimated from the query image IA4 is an equilibrium phase.

It is provided that the layout information L1 stored in the storage area DA arranges two of similar images corresponding to the plain CT, the arterial phase, the portal phase, and the equilibrium phase from the left to the right along the horizontal direction on the display screen of the display unit 5, and repeats this arrangement from the top to the bottom in the vertical direction on the display screen (horizontal scanning), thereby specifying to arrange four similar images included in one similar image group in a 2×2 square lattice format.

Figure 4:
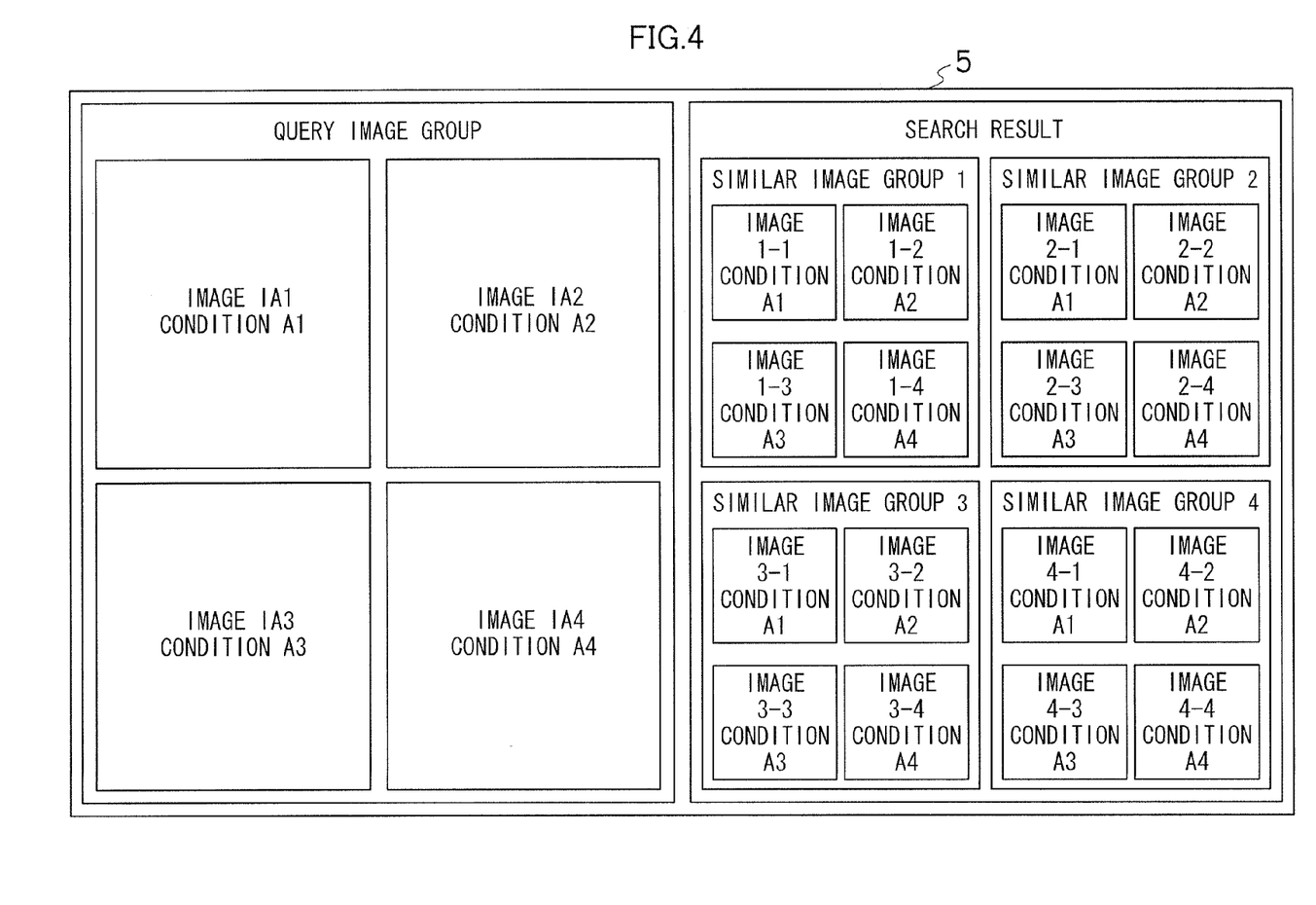
FIG. 4 is a diagram illustrating a first example of a screen arrangement for displaying a similar image group.

In this case, as shown in FIG. 4, the individual similar images in the similar image group (instead of one, a plurality of similar image groups may be displayed) similar to the query image groups IA1 to IA4 retrieved from the storage area DA corresponding to the region IA are arranged on the display screen of the display unit 5 according to the layout information L1 corresponding to the storage area DA.

Further, the layout information specifies a planar arrangement of the query image group conformable to the planar arrangement of the case image group.

For example, as shown in FIG. 4, by the layout information L1, the planar arrangement of the query image group IA1 to IA4 and a planar arrangement of the individual images IA1 to IA4 in the similar image group similar to the respective images IA1 to IA4 in the query image group is conformed to the 2×2 square lattice format. In FIG. 4, according to the layout information L1, the query image group IA is arranged in a left half region on the display screen of the display unit 5, and the similar image groups are arranged in a right half region of the display screen. However, these arrangements may be interchanged. With respect to both image groups, the arrangements are conformed by sequentially arranging the images from the left to the right along the horizontal direction of the display screen of the display unit 5 and repeating this arrangement from the top to the bottom in the vertical direction on the display screen. If there are a plurality of similar image groups, the plurality of image groups can be displayed in the right half region on the display screen in a uniform size and the identical planar arrangement. However, the size of the individual similar image and the size of the query image may be different from each other.

An arrangement rule specified by the layout information is arbitrary. Vertical scanning is acceptable instead of horizontal scanning. A vertical assembly and a horizontal assembly are acceptable.

Figure 5A:
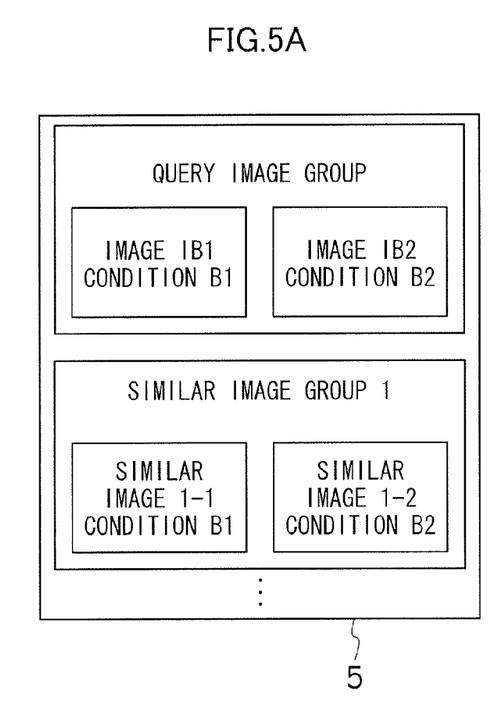
FIGS. 5A and 5B are diagrams illustrating a second example for displaying a similar image group.
Figure 5B:
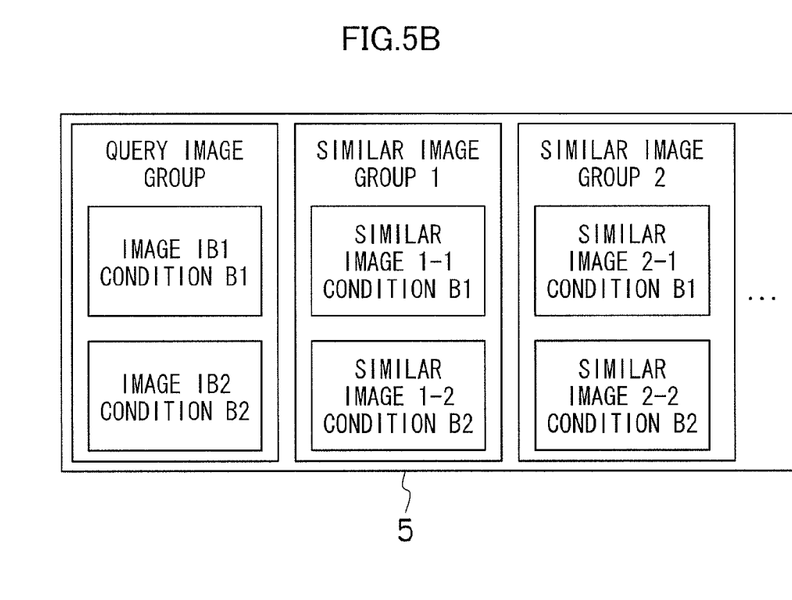

For example, it is assumed that the estimated region is the lungs, the estimated imaging conditions are a lung field condition B1 and a mediastinum condition B2. In this case, as illustrated in FIGS. 5A and 5B, the query images IB1 and IB2 and the similar image group IB1' and IB2' corresponding to two imaging conditions B1 and B2 are displayed in parallel and opposition. This arrangement may be a horizontal assembly (FIG. 5A) or a vertical assembly (FIG. 5B). When a plurality of the similar image groups are arranged in the horizontal assembly, the query image group is arranged in the top region in the vertical direction and the similar image groups are sequentially arranged in descending order of the rank, from the query image group, downwardly in the vertical direction. When a plurality of similar image groups are arranged in the vertical assembly, the query image group is arranged in the left region and the similar image groups are arranged in the descending order of the rank, from the query image groups, rightwardly in the horizontal direction.

Since the individual query images in the query image group and the individual similar images in the similar image group are thus arranged in opposition with respect to each imaging condition, comparison between the query images and the similar images corresponding to the identical condition is facilitated.

As illustrated in FIGS. 4, 5A and 5B, a screen where the individual query images in the query image group and the individual similar images in the similar image group conform to each other is referred to as an initial search result screen.

Further, it is not necessarily to display all the individual query images in the query image group and all the individual similar images in the similar image. Instead, the query images and the similar images corresponding to a specific imaging condition may be displayed.

Figure 6:
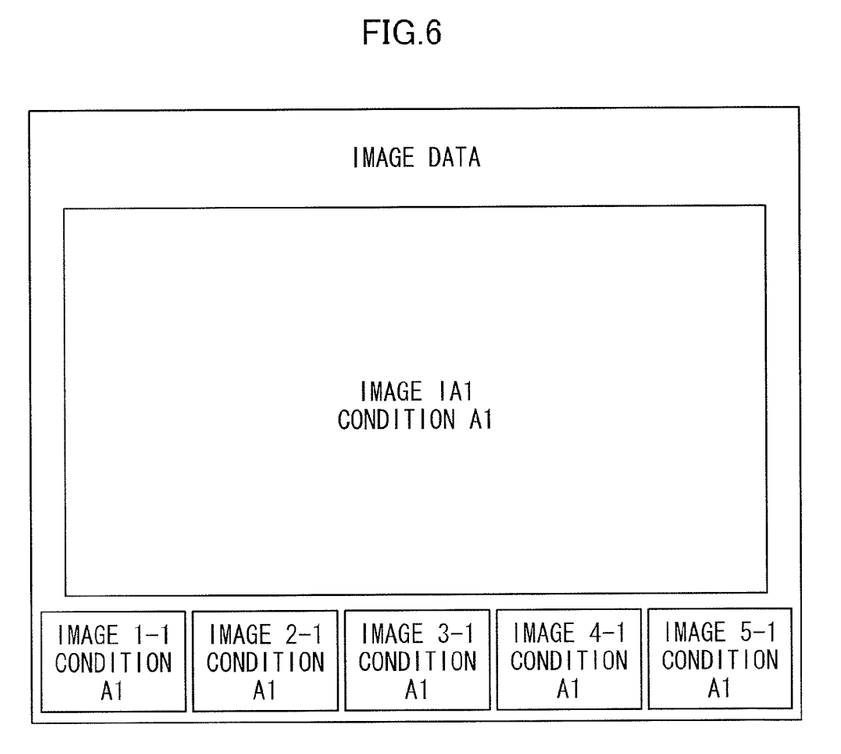
FIG. 6 is a diagram illustrating a third example of a screen arrangement for displaying a similar image group.

For example, as illustrated in FIG. 6, the query image corresponding to the imaging condition A1 is arranged in an upper region of the screen, and the similar images corresponding to the imaging condition A1 are arranged in a lower region of the screen. The screen having such an arrangement is referred to as an imaging condition-specific result display screen. In FIG. 6, the size of the query image is larger than that of the similar image. However, the size of the query image may be identical to or smaller than that of the similar image. It is arbitrary which condition to be focused on to create the imaging condition-specific result display screen. For example, when the query image corresponding to a specific imaging condition (e.g., A1) is designated on the initial search result display screen as illustrated in FIG. 4 and FIGS. 5A and 5B through the operation device, the screen transitions to the imaging condition-specific result display screen including the designated query image and the similar images corresponding to the designated imaging condition (e.g., A1); the screen is displayed as in FIG. 6. Instead, without displaying the initial search result display screen itself, the imaging condition-specific result display screen corresponding to the preliminarily designated imaging condition may be displayed, and the imaging condition-specific result display screen may transition to the initial search result display screen responsive to designation of "Display initial search result display screen" inputted from the operation device. The initial search result display screen and the imaging condition-specific result display screen may be interchanged.

Figure 7:
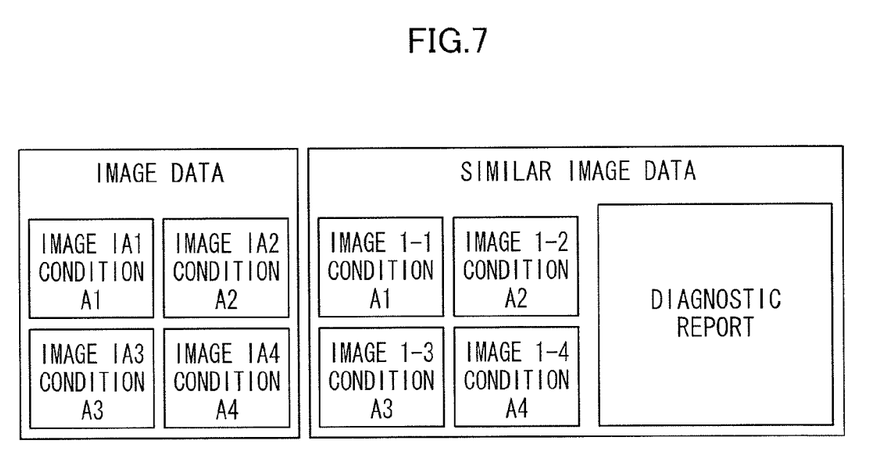
FIG. 7 is a diagram illustrating an example of a screen arrangement for displaying a similar image group and a diagnostic report.

Further, a diagnostic report and another piece of diagnostic information corresponding to the similar image group may be displayed. For example, when any similar image group is designated on the initial search result display screen as illustrated in FIGS. 4, 5A and 5B through the operation device, the diagnostic report or another piece of diagnostic information accompanying the designated similar image group can be displayed as illustrated in FIG. 7. The similar image groups having not been designated may be eliminated from the initial search result display screen in order to expand a space for displaying the diagnostic information. Instead, the diagnostic information may be displayed in a pop-up display without elimination of the similar images having not been designated from the initial search result display screen. A method for designating the similar image group is arbitrary; the similar image group may be designated by overlapping a mouse pointer with the similar image group or clicking or double-clicking the similar image group with a mouse. Further, three-sectional images in an axial, a sagittal and a coronal directions, volume rendering images or the like generated as a three-dimensional model from the similar image group may be displayed independent from or along with the similar image group. Here, the maximum number of images to be displayed in one screen of the display unit 5 may be designated through the operation device, and the designated number of images may be displayed.

As described above, in the similar case search system 100, the region analysis unit 21 and the imaging condition analysis unit 22 estimate the region and the imaging condition, respectively, from the received query image, and the similarity value calculation unit 31 retrieves the case image corresponding to the estimated region and the estimated imaging condition and displays the retrieved case image. Accordingly, it is not necessary to designate the imaged region and the imaging condition of the query image by a manual operation, thereby improving efficiency.

The presently disclosed subject matter can be provided as a computer-readable program code for causing a computer to execute the above described process, a computer-readable recording medium on which the computer-readable program code is stored or a computer program product including the computer-readable program code.

What is claimed is:

1. A case image search apparatus comprising:
   an input unit for inputting a diagnostic object image group from an imaging apparatus;
   an estimation unit for estimating attributes of a diagnostic object image included in the diagnostic object image group on the basis of the diagnostic object image;
   a calculation unit for calculating a first feature amount which is a feature amount of the diagnostic object image corresponding to the attribute estimated by the estimation unit; and
   a search unit for searching a database for a similar case image group similar to the diagnostic object image group by comparing the first feature amount with a second feature amount which is a feature amount of a case image included in the case image group stored in the database corresponding to the attribute estimated by the estimation unit.

2. The case image search apparatus according to claim 1, wherein the attribute includes information indicating an imaged region of the diagnostic object image.

3. The case image search apparatus according to claim 2, wherein the estimation unit estimates the imaged region on the basis of a feature amount pertaining to a pixel value and a shape of the diagnostic object image.

4. The case image search apparatus according to claim 1, wherein the attribute includes information indicating an imaging condition of the diagnostic object image.

5. The case image search apparatus according to claim 4, wherein the imaging condition includes information indicating with or without contrast material, or temporal phases of multi-phase imaging.

6. The case image search apparatus according to claim 1, wherein the search unit searches the database for the similar case image group by comparing the feature amount pertaining to at least one of the pixel value and the shape of the diagnostic object image with the feature amount pertaining to at least one of the pixel value and the shape of the case image.

7. The case image search apparatus according to claim 6, further comprising a selection unit for selecting a lesion region from the diagnostic object image,
   wherein the search unit searches the database for the similar case image group on the basis of the feature amount pertaining to the lesion region selected by the selection unit.

8. The case image search apparatus according to claim 7, wherein the selection unit selects the lesion region on the basis of the amount of the feature pertaining to at least one of the pixel value and the shape of the diagnostic object image.

9. The case image search apparatus according to claim 1, further comprising a display unit for displaying the similar case image group searched by the search unit.

10. The case image search apparatus according to claim 9, wherein the database stores supplementary information corresponding to the case image, and
    the display unit displays the supplementary information of the database corresponding to the case image included in the similar case image group.

11. The case image search apparatus according to claim 9, wherein the display unit specifies a screen layout of the similar case image group corresponding to the attribute estimated by the estimation unit.

12. The case image search apparatus according to claim 1, wherein the input unit inputs the diagnostic object image group from a CT, an MRI or another medical imaging apparatus.

13. The case image search apparatus according to claim 1, wherein the calculation unit calculates the first feature amount using a computational expression corresponding to the attribute estimated by the estimation unit.

14. A case image search method causing a computer to perform the steps of:
    inputting a diagnostic object image group from an imaging apparatus;
    estimating attributes of a diagnostic object image included in the diagnostic object image group on the basis of the diagnostic object image;
    calculating a first feature amount which is a feature amount of the diagnostic object image corresponding to the estimated attribute; and
    searching a database for a similar case image group similar to the diagnostic object image group by comparing the first feature amount with a second feature amount which is a feature amount of the case image in the database corresponding to the estimated attribute.

15. A non-transitory computer-readable recording medium including instructions stored thereon, such that when the instructions are read and executed by a processor, the processor is configured to perform the steps of:
    inputting a diagnostic object image group from an imaging apparatus;
    estimating attributes of a diagnostic object image included in the diagnostic object image group on the basis of the diagnostic object image;
    calculating a first feature amount which is a feature amount of the diagnostic object image corresponding to the estimated attribute; and
    searching a database for a similar case image group similar to the diagnostic object image group by comparing the first feature amount with a second feature amount which is a feature amount of the case image in the database corresponding to the estimated attribute.

* * * * *